United States Patent
Dong et al.

[11] Patent Number: 5,769,856
[45] Date of Patent: Jun. 23, 1998

[54] DRILL GUIDE AND IMPLANT METHOD

[75] Inventors: Nicholas N. G. Dong, Little Falls; Peter J. Abitante, Westfield, both of N.J.

[73] Assignee: Osteonics Corp., Allendale, N.J.

[21] Appl. No.: 669,078

[22] Filed: Jun. 24, 1996

[51] Int. Cl.[6] .................................................. A61F 5/04
[52] U.S. Cl. ........................................... 606/96; 606/80
[58] Field of Search .................................. 606/96, 97, 98, 606/99, 104, 91, 79, 86; 623/19

[56] References Cited

U.S. PATENT DOCUMENTS

| | | | |
|---|---|---|---|
| D. 284,889 | 7/1986 | Kenna | D24/26 |
| 5,030,219 | 7/1991 | Matsen, III et al. | 606/53 |
| 5,080,673 | 1/1992 | Burkhead et al. | 623/19 |
| 5,112,336 | 5/1992 | Krevolin et al. | 606/96 |
| 5,462,550 | 10/1995 | Dietz et al. | 606/86 |

FOREIGN PATENT DOCUMENTS

| | | | |
|---|---|---|---|
| 499475 | 8/1992 | European Pat. Off. | 606/91 |
| 2041929 | 10/1980 | Germany | 623/19 |

OTHER PUBLICATIONS

DePuy Inc. "Components and Instruments," (date unknown).
Morrey, Bernard. "Joint Replacement Arthroplasty," (1991), Churchill Livingstone, p. 432.
Petty, William. "Total Joint Replacement," (1991), W.B. Saunders Company, p. 630–631.
DePuy Inc. "Global Total Shoulder Arthroplasty System," (1994), pp. 18–19.
Intermedics Orthopedics, Inc. "The Intermedics Select Shoulder System," (1992), pp. 22–23.
Biomet, Inc. "Bio–Modular Total Shoulder," (1995), Steps 8–9B.
Smith & Nephew Richards, Inc. "The Cofield Total Shoulder System," (date unknown), Fig. 13–16.

*Primary Examiner*—Michael Buiz
*Assistant Examiner*—Julian W. Woo
*Attorney, Agent, or Firm*—Arthur Jacob

[57] ABSTRACT

Apparatus and method for locating holes to be drilled in natural bone, such as a scapula at a site for a prosthetic implant component, such as a glenoid component to be affixed to the scapula for providing a bearing for a humeral head in a shoulder prosthesis, the apparatus and method including seating a guide block against the scapula at the site for the glenoid component, the guide block having an upper end and a lower end spaced in a longitudinal direction from the upper end, drilling a first hole in the scapula along a first transverse direction by guiding a drill through a first drill guide bore adjacent the upper end of the guide block and extending in the first transverse direction through the guide block, the guide block including a second drill guide bore adjacent the lower end of the guide block and extending in a second transverse direction through the guide block, inserting a locator pin into the first hole in the scapula, with the locator pin projecting from the guide block along one of the first and second transverse directions for reception within the first hole along the first transverse direction, and seating the guide block on the scapula to locate the second transverse direction relative to the scapula, and drilling a second hole in the scapula along the second transverse direction by guiding a drill through the second drill guide bore.

22 Claims, 5 Drawing Sheets

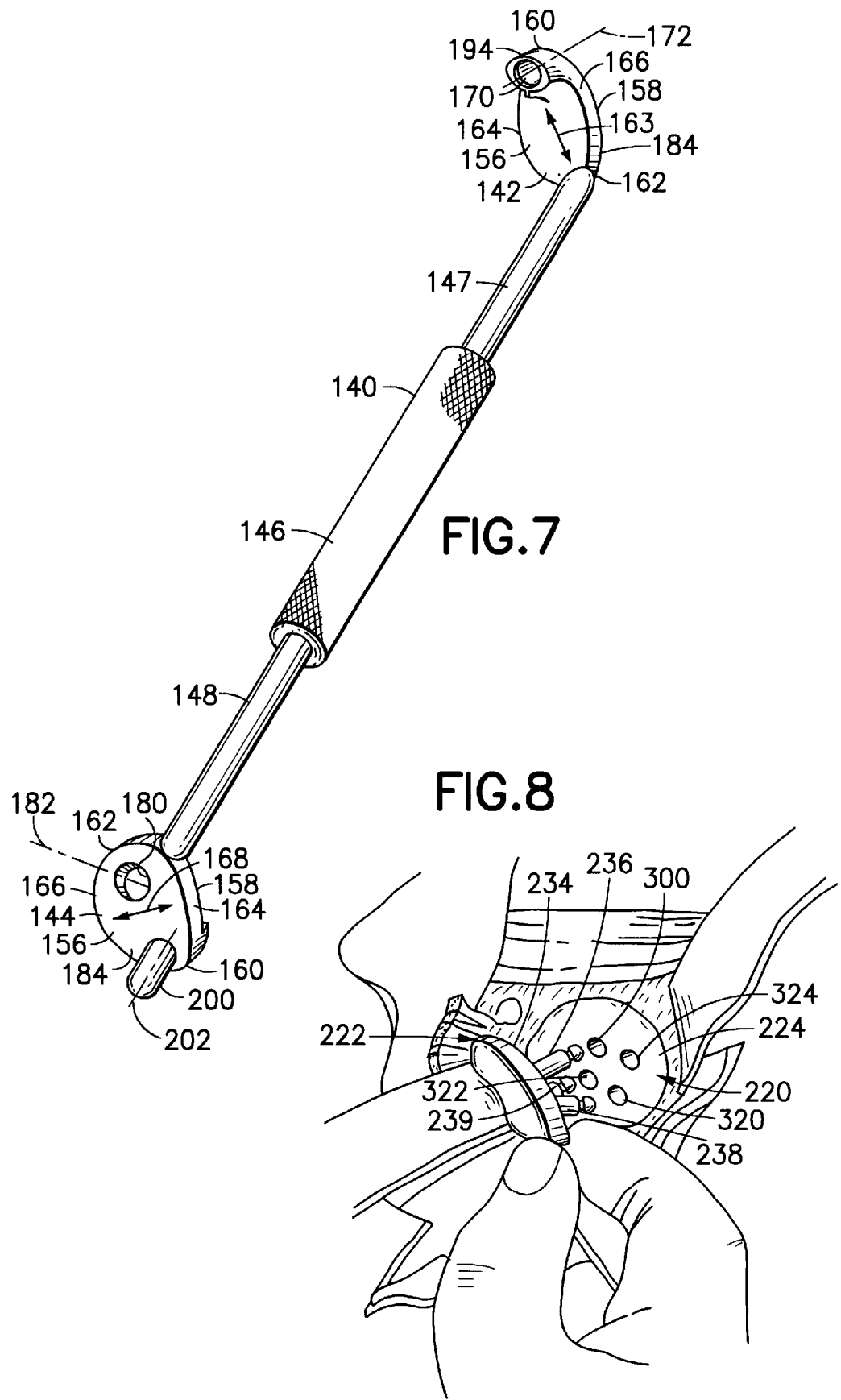

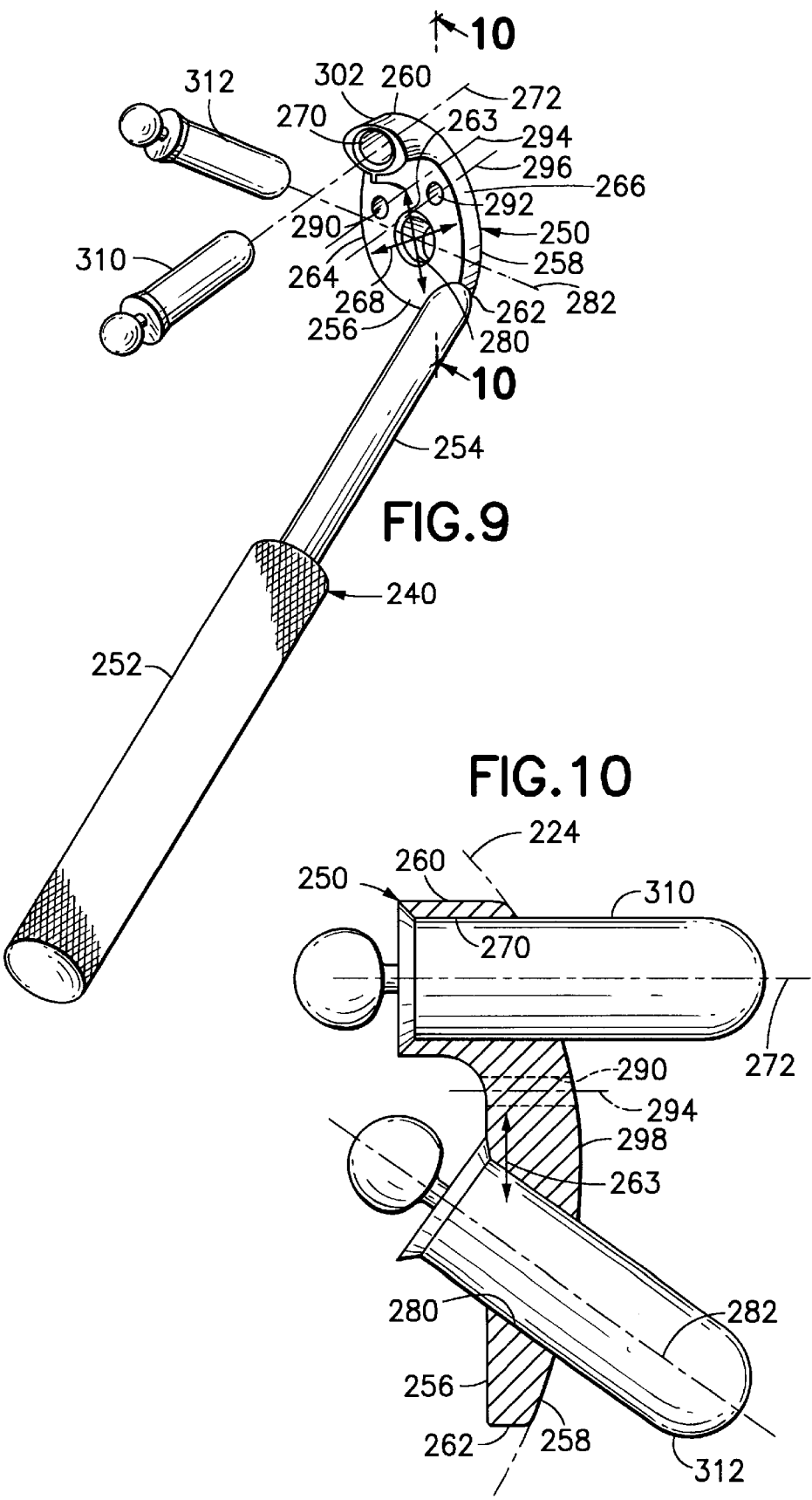

DRILL GUIDE AND IMPLANT METHOD

The present invention relates generally to the implant of orthopedic prostheses and pertains, more specifically, to a drill guide and a method for assisting in the placement and affixation of a glenoid component of a shoulder prosthesis in a scapula at an implant site.

Shoulder arthroplasty has become a highly successful procedure, and a variety of components is available for the implant of shoulder prostheses. Despite the success of the procedure, the incidence of separation of the glenoid component of a shoulder prosthesis from the scapula remains relatively high. Consequently, improved prostheses and implant instruments and procedures continue to be developed in an effort to avoid such occurrences. Accordingly, an improved glenoid component and procedure are described in United States patent application Ser. No. 08/555,720, filed Nov. 14, 1995, now U.S. Pat. No. 5,593,448, the disclosure of which is incorporated herein by reference thereto, and the present invention provides a drill guide and method for assisting in the appropriate location and affixation of the glenoid component at the implant site.

As such, the present invention attains several objects and advantages, some of which are summarized as follows: Facilitates the location and drilling of holes in the natural bone at the site of a prosthetic implant for appropriate placement and seating of a prosthetic implant component having a specific array of affixation pegs, and especially in connection with the drilling of holes in a scapula for the implant of a glenoid component of a shoulder prosthesis; accommodates the array of affixation pegs in an effective and efficient manner, enabling a reduction in the time necessary to complete an implant procedure, to the benefit of the recipient of the implant; attains increased accuracy with increased ease; provides simplified instruments and procedures for attaining improved results; enables more economical manufacture of effective instruments having a rugged construction for exemplary performance over an extended service life.

The above objects and advantages, as well as further objects and advantages, are attained by the present invention which may be described briefly as a drill guide for locating holes to be drilled in the natural bone at a site for a prosthetic implant component to be affixed to the natural bone, with the holes arranged in an array complementary to an array of affixation pegs projecting from the prosthetic implant component, the drill guide comprising: a guide block having an obverse face and a reverse face, an upper end and a lower end spaced in a longitudinal direction from the upper end, and opposite side edges spaced in lateral directions from one another; a first drill guide bore adjacent the upper end of the guide block and extending in a first transverse direction, transverse to the longitudinal and lateral directions, through the guide block from the obverse face to the reverse face, for guiding a drill to drill a first hole in the natural bone along the first transverse direction when the reverse face of the guide block is seated against the natural bone at the site for the prosthetic implant component; a second drill guide bore adjacent the lower end of the guide block and extending in a second transverse direction, transverse to the longitudinal and lateral directions, through the guide block from the obverse face to the reverse face, for guiding a drill to drill a second hole in the natural bone along the second transverse direction when the reverse face of the guide block is seated against the natural bone at the site for the prosthetic implant component; at least one locator pin for projecting from the reverse face of the guide block along at least one of the first and second transverse directions for reception within at least one of the first and second holes drilled in the natural bone along a corresponding one of the first and second transverse directions to place the guide block on the natural bone and locate the other of the first and second transverse directions for drilling the other of the first and second holes in the natural bone along the other of the first and second transverse directions, such that the first and second holes are arranged in an array corresponding to the first and second transverse directions and complementary to the array of the affixation pegs of the prosthetic implant component.

In addition, the invention includes a method for implanting a prosthetic implant component, the method including locating holes to be drilled in the natural bone at a site for the prosthetic implant component, the prosthetic implant component including affixation pegs projecting from the prosthetic implant component in an array, the method comprising: seating the reverse face of a guide block against the natural bone at the site for the prosthetic implant component, the guide block having an obverse face and a reverse face, an upper end and a lower end spaced in a longitudinal direction from the upper end, and opposite side edges spaced in lateral directions from one another; drilling a first hole in the natural bone along a first transverse direction by guiding a drill through a first drill guide bore adjacent the upper end of the guide block and extending in the first transverse direction transverse to the longitudinal and lateral directions, through the guide block from the obverse face to the reverse face, the guide block including a second drill guide bore adjacent the lower end of the guide block and extending in a second transverse direction transverse to the longitudinal and lateral directions, through the guide block from the obverse face to the reverse face; inserting a locator pin into the first hole in the natural bone, with the locator pin coupled with the guide block and projecting from the reverse face of the guide block along one of the first and second transverse directions for reception within the first hole along the first transverse direction, and the reverse face of the guide block seated on the natural bone to locate the second transverse direction relative to the natural bone; drilling a second hole in the natural bone along the second transverse direction by guiding a drill through the second drill guide bore such that the first and second holes are arranged in an array corresponding to the first and second transverse directions and complementary to the array of the affixation pegs of the prosthetic implant component; retracting the guide block from the natural bone; and affixing the prosthetic implant component to the natural bone at the site, with the affixation pegs inserted into the first and second holes.

The invention will be understood more fully, while still further objects and advantages will become apparent, in the following detailed description of preferred embodiments of the invention illustrated in the accompanying drawing, in which:

FIG. 7 is a perspective view of another glenoid drill guide constructed in accordance with the present invention;

FIG. 8 is a pictorial perspective showing an alternate glenoid component of a shoulder prosthesis being affixed to a scapula at an implant site;

FIG. 9 is a perspective view of still another glenoid drill guide constructed in accordance with the invention; and FIG. 10 is an enlarged cross-sectional view taken along line 10—10 of FIG. 9.

Figure 1:
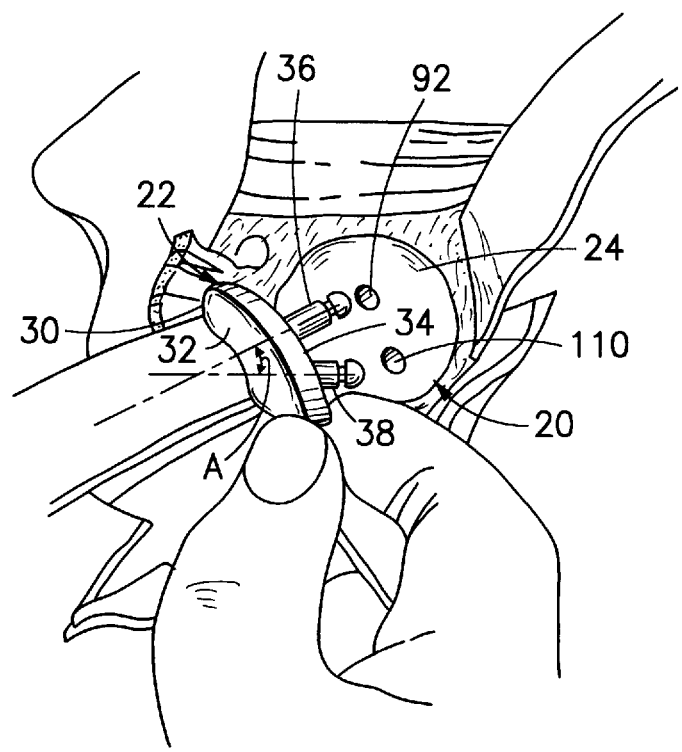
FIG. 1 is a pictorial perspective view showing a glenoid component of a shoulder prosthesis being affixed to a scapula at an implant site.

Referring now to the drawing, and especially to FIG. 1 thereof, a scapula 20 has been prepared for the affixation of a glenoid component 22 of a shoulder prosthesis to the scapula 20 at the glenoid surface 24 of the scapula 20, which is the site for the glenoid component 22. As described more fully in the aforesaid application Ser. No. 08/555,720, glenoid component 22 includes a glenoid member 30 extending in superior-inferior directions, that is, in upward and downward directions, and provides a bearing surface 32 for a humeral head (not shown). Glenoid component 22 has an affixation surface 34 for affixing the glenoid component 22 to the scapula 20. An upper, or superior affixation peg 36 and a lower, or inferior affixation peg 38 project from the affixation surface 34 to assist in securing the glenoid component 22 in place on the scapula 20. The lower affixation peg 38 is oriented in an offset direction relative to the upper affixation peg 36, the offset direction making an acute angle A with the direction of the upper affixation peg 36. In the preferred orientation, angle A is about 30°.

Figure 2:
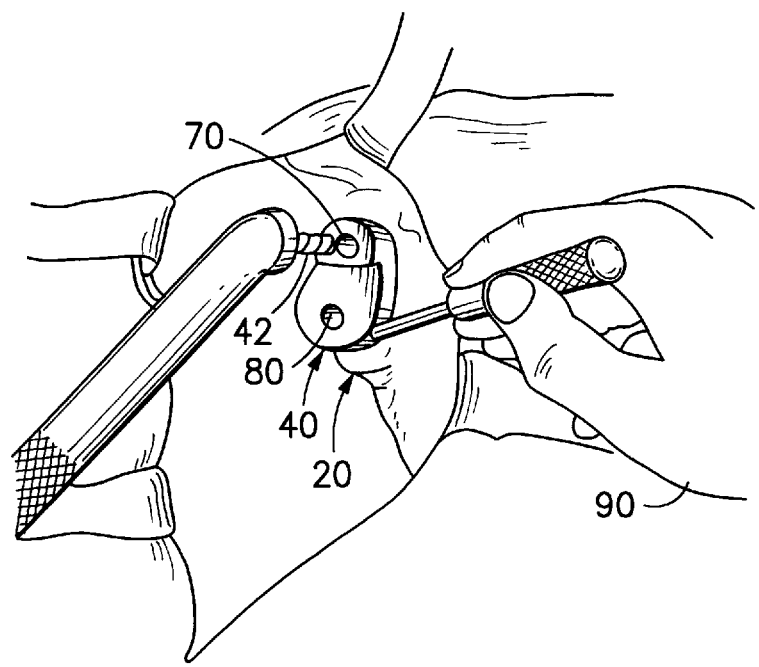
FIG. 2 is a pictorial perspective view showing the drilling of a hole in the scapula in connection with preparation of the scapula for the implant of the glenoid component in accordance with the present invention.

The scapula 20 has been prepared to receive the affixation pegs 36 and 38 by drilling counterpart holes in the scapula 20 for reception of the pegs 36 and 38. As illustrated in FIG. 2, a drill guide 40 is constructed in accordance with the present invention and is shown in place against the scapula 20 for locating holes to be drilled in the scapula 20 with a drill 42, guided by the drill guide 40.

Figure 3:
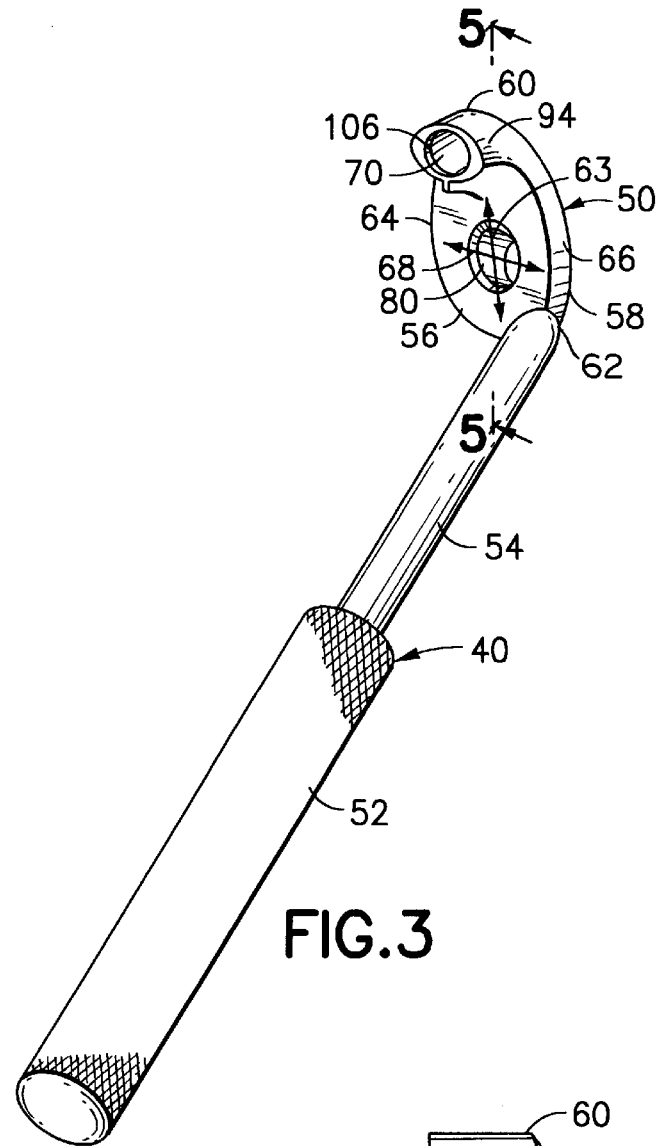
FIG. 3 is a perspective view of a glenoid drill guide constructed in accordance with the present invention.
Figure 4:
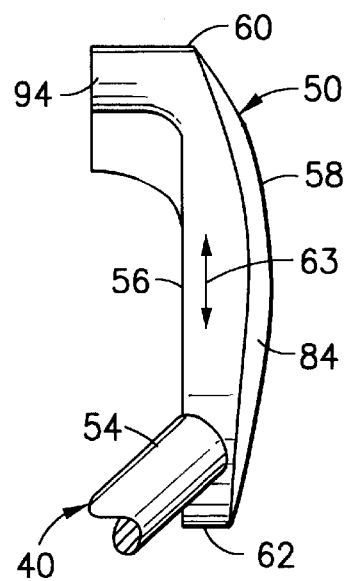
FIG. 4 is an enlarged side view of a portion of the glenoid drill guide.
Figure 5:
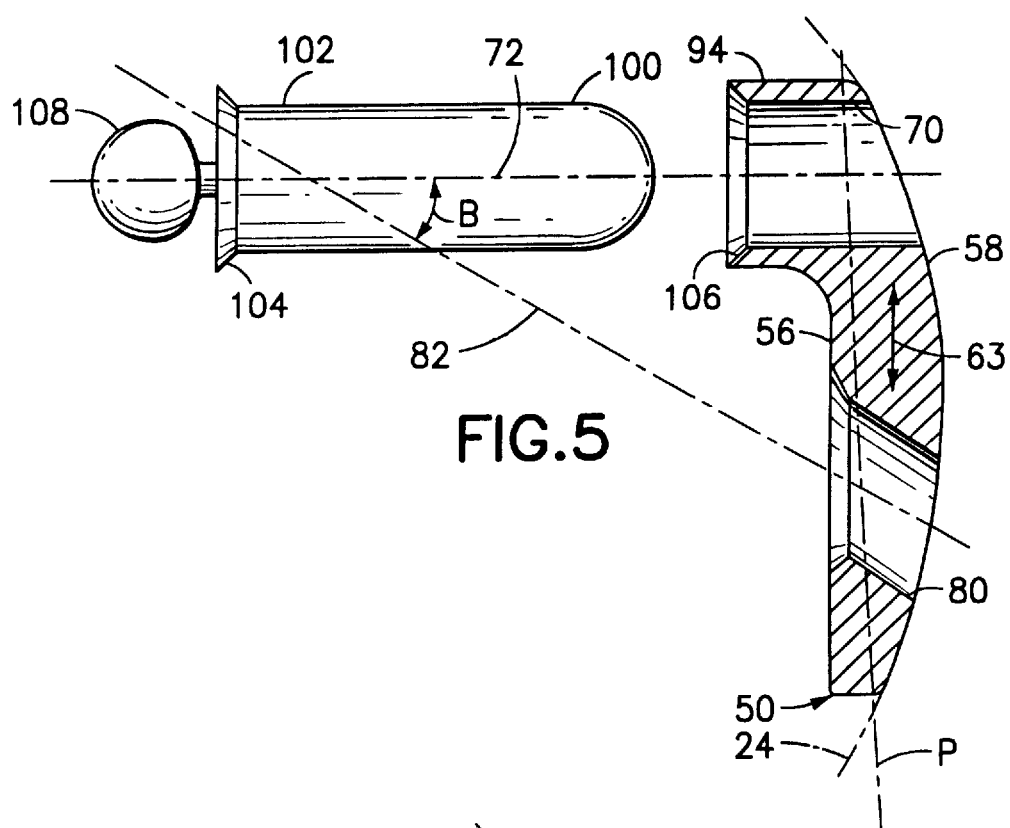
FIG. 5 is an enlarged cross-sectional view taken along line 5—5 of FIG. 3.

Turning now to FIGS. 3 through 5, drill guide 40 is seen to include a guide block 50 and a handle 52 attached to the guide block 50 through a shaft 54 which extends between the guide block 50 and the handle 52. Guide block 50 includes an obverse face 56 and a reverse face 58, an upper end 60 and a lower end 62 spaced from one another in longitudinal directions 63 and opposite side edges 64 and 66 spaced from one another in lateral directions 68. A first drill guide bore 70 is located adjacent the upper end 60 and, as best seen in FIG. 5, extends through the guide block 50, from the obverse face 56 to the reverse face 58, along a first transverse direction 72, the transverse direction 72 being transverse to the longitudinal directions 63 and the lateral directions 68. A second drill guide bore 80 is located adjacent the lower end 62 of the guide block 50, spaced longitudinally from the first drill guide bore 70, and extends through the guide block 50 from the obverse face 56 to the reverse face 58, along a second transverse direction 82, the transverse direction 82 being transverse to the longitudinal directions 63 and the lateral directions 68.

As best seen in FIGS. 4 and 5, the reverse face 58 of the guide block 50 includes a surface 84 having a surface contour configuration generally complementary to the glenoid surface 24 of the scapula 20, at the site where the glenoid component 22 is to be affixed to the scapula 20. The reverse face 58 is placed against the glenoid surface 24, as illustrated in FIG. 2, as well as in FIG. 5, by a surgeon 90 who holds the drill guide 40 by the handle 52, as seen in FIG. 2, and then guides the drill 42 through the first drill guide bore 70 to drill a first hole 92 (see FIG. 1) in the scapula 20.

In order to enhance support of the drill 42 during the drilling of the first hole 92, and thus increase the accuracy with which the first hole 92 is drilled, the guide block 50 is provided with a sleeve portion 94 which extends from the obverse face 56 in a direction opposite to the first transverse direction 72 and extends the first drill guide bore 70 for increased support of the drill 42 in accurate alignment with first transverse direction 72.

Figure 6:
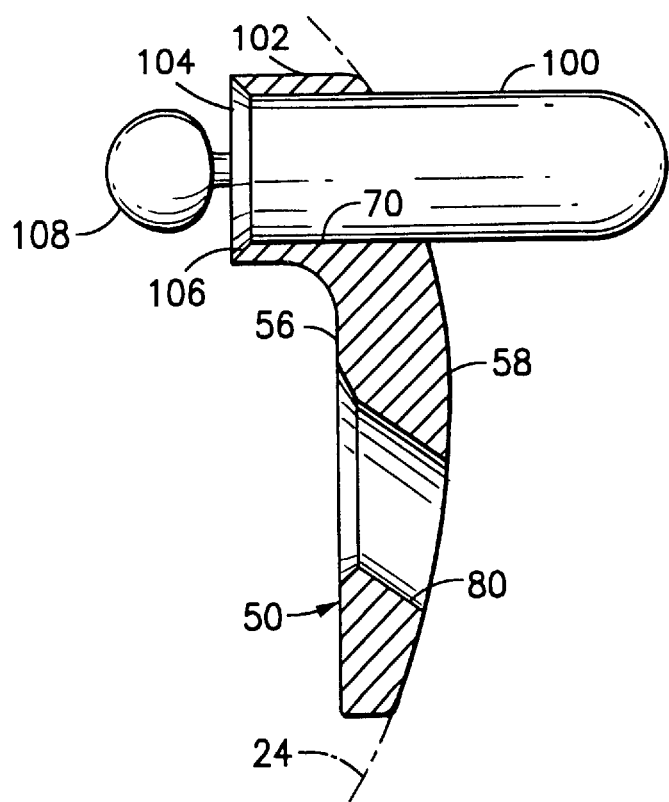
FIG. 6 is a cross-sectional view similar to FIG. 5, showing the component parts in another position.

Once the first hole 92 is completed, a locator pin 100 is coupled with the guide block 50 to project from the reverse face 58, along the first transverse direction 72, as shown in FIG. 6. To that end, coupling means are provided for selectively detachably coupling the locator pin 100 with the guide block 50, the coupling means including a generally cylindrical plug portion 102 on the locator pin 100 complementary to the first drill guide bore 70 for reception in the first drill guide bore 70 to attach the locator pin 100 to the guide block 50. In the preferred procedure, the locator pin 100 is advanced through the first drill guide bore 70 in the direction from the obverse face 56 toward the reverse face 58, along the first transverse direction 72, while the surface 84 of the guide block 50 is maintained seated against the glenoid surface 24. Upon completing the attachment of the locator pin 100 to the guide block 50, a flange 104 on the locator pin 100 is seated within a complementary recess 106 at the drill guide bore 70 and the distal, or far end of the locator pin 100 extends into the first hole 92. A grip 108 is provided at the proximal, or near end of the locator pin 100 for facilitating the selective attachment and detachment of the locator pin 100 and the guide block 50. In this manner, the second drill guide bore 80 is located in place accurately relative to the first hole 92 for the drilling of a second hole 110 (see FIG. 1) in the scapula 20. The surgeon 90 then guides the drill 42 through the second drill guide bore 80 to drill the second hole 110 (see FIG. 1) in the scapula 20, along the second transverse direction 82.

As best seen in FIG. 5, the second transverse direction 82 is oriented relative to the first transverse direction 72 at an acute angle B, with the first and second transverse directions 72 and 82 diverging in the direction from the obverse face 56 toward the reverse face 58. The longitudinal and lateral directions 63 and 68 essentially lie in a plane P and the first transverse direction 72 extends essentially normal to the plane P. Acute angle B essentially is the same as acute angle A. Thus, the size, orientation and placement of the first and second holes 92 and 110 places the first and second holes 92 and 110 in an array corresponding to the first and second transverse directions 63 and 68, and complements the size, orientation and placement of the array of affixation pegs 36 and 38 of the glenoid component 22 for a high degree of accuracy in the location and affixation of the glenoid component 22 at the glenoid surface 24 of the scapula 20.

Turning now to FIG. 7, another glenoid drill guide constructed in accordance with the invention is illustrated at 140 and is seen to include a first guide block 142 and a second guide block 144, with a common handle 146 between the guide blocks 142 and 144 and attached to the guide blocks 142 and 144 through corresponding respective shafts 147 and 148. Glenoid drill guide 140 is used for the same purpose as glenoid drill guide 40, that is, the scapula 20 is to be prepared with two holes 92 and 110 sized, placed and oriented to receive the two affixation pegs 36 and 38 of the glenoid component 22, with the assistance of the drill guide 140; however, as is evident, the construction of the drill guide 140 differs in some respects from the construction of drill guide 40, with a concomitant difference in procedure.

Thus, each guide block 142 and 144 has a basic overall configuration very similar to guide block 50 in that each guide block 142 and 144 includes an obverse face 156 and a reverse face 158, an upper end 160 and a lower end 162 spaced from one another in longitudinal directions 163 and opposite side edges 164 and 166 spaced from one another in lateral directions 168. A first drill guide bore 170 is located adjacent the upper end 160 of the first guide block 142 and extends through the first guide block 142, from the obverse face 156 to the reverse face 158, along a first transverse direction 172, the transverse direction 172 being transverse to the longitudinal directions 163 and the lateral directions 168. A second drill guide bore 180 is located adjacent the lower end 162 of the second guide block 144 and extends through the second guide block 144 from the obverse face 156 to the reverse face 158, along a second transverse direction 182, the transverse direction 182 being transverse to the longitudinal directions 163 and the lateral directions 168.

The reverse face 158 of each guide block 142 and 144 includes a surface 184 having a surface contour configuration generally complementary to the glenoid surface 24 of the scapula 20, at the site where the glenoid component 22 is to be affixed to the scapula 20. In a procedure somewhat similar to that described above in connection with drill guide 40, the reverse face 158 of the first guide block 142 is placed against the glenoid surface 24, and the drill guide 140 is held in place by the handle 146, while a drill is guided through the first drill guide bore 170 to drill the first hole 92 in the scapula 20. In order to enhance support of the drill during the drilling of the first hole 92, and thus increase the accuracy with which the first hole 92 is drilled, the guide block 142 is provided with a sleeve portion 190 which extends from the obverse face 156 in a direction opposite to the first transverse direction 172 and extends the first drill guide bore 170 for increased support of the drill in accurate alignment with first transverse direction 172.

Once the first hole 92 is completed, the first guide block 142 is retracted from the scapula 20 and the second guide block 144 is placed against the scapula 20, with the reverse face 158 seated against the glenoid surface 24. A locator pin 200 integral with the second guide block 144 and projecting from the reverse face 158 of the second guide block 144 is inserted into the first hole 92 so as to locate the second drill guide bore 180 in place for the drilling of the second hole 110 in the scapula 20. A drill is guided through the second drill guide bore 180 to drill the second hole 110 along the second transverse direction 182. The orientation and location of the locator pin 200 relative to the second drill guide bore 180, along a transverse direction 202, which corresponds to the first transverse direction 172, locates the second drill guide bore 180 in position to place the second hole 110 relative to the first hole 92 for appropriate reception of the affixation pegs 36 and 38 of the glenoid component 22. Thus, the size, orientation and placement of the first and second holes 92 and 110 complements the size, orientation and placement of the affixation pegs 36 and 38 of the glenoid component 22 for a high degree of accuracy in the location and affixation of the glenoid component 22 at the glenoid surface 24 of the scapula 20. Since the locator pin 200 already is integral with the second guide block 144, use of the drill guide 140, rather than the drill guide 40, eliminates the need to couple a separate locator pin with the guide block, as described above in connection with the use of drill guide 40. Further, the surgeon need hold only a single drill guide 140 which merely is reversed end-to-end during the procedure to accomplish the drilling of both holes 92 and 110.

Referring now to FIG. 8, a scapula 220 has been prepared for the affixation of a glenoid component 222 of a shoulder prosthesis to the scapula 220 at the glenoid surface 224 of the scapula 220, in very much the same manner as described above in connection with the first embodiment of the present invention. That is, glenoid component 222 has an affixation surface 234 for affixing the glenoid component 222 to the scapula 220, and an upper, or superior affixation peg 236 and a lower, or inferior affixation peg 238 project from the affixation surface 234 to assist in securing the glenoid component 222 in place on the scapula 220. However, glenoid component 222 includes intermediate affixation pegs 239 placed intermediate the superior and inferior affixation pegs 236 and 238, extending generally parallel to the upper affixation peg 236, and spaced apart in the anterior-posterior direction. The scapula 220 has been prepared to receive the affixation pegs 236, 238, and 239 by drilling counterpart holes in the scapula 220 for reception of the pegs 236, 238 and 239.

Turning now to FIGS. 9 and 10, a drill guide 240 constructed in accordance with the invention is seen to include a guide block 250 and a handle 252 attached to the guide block 250 through a shaft 254 which extends between the guide block 250 and the handle 252. As before, guide block 250 includes an obverse face 256 and a reverse face 258, an upper end 260 and a lower end 262 spaced from one another in longitudinal directions 263 and opposite side edges 264 and 266 spaced from one another in lateral directions 268. A first drill guide bore 270 is located adjacent the upper end 260 and, as best seen in FIG. 10, extends through the guide block 250, from the obverse face 256 to the reverse face 258, along a first transverse direction 272, the transverse direction 272 being transverse to the longitudinal directions 263 and the lateral directions 268. A second drill guide bore 280 is located adjacent the lower end 262 of the guide block 250 and extends through the guide block 250 from the obverse face 256 to the reverse face 258, along a second transverse direction 282, the transverse direction 282 being transverse to the longitudinal directions 263 and the lateral directions 268. Third and fourth drill guide bores 290 and 292 are located each adjacent one of the side edges 264 and 266 of the guide block 250 and extend through the guide block 250, from the obverse face 256 to the reverse face 258, along corresponding transverse directions 294 and 296, essentially parallel to the first transverse direction 272.

As best seen in FIG. 10, the reverse face 258 of the guide block 250 includes a surface 298 having a surface contour configuration generally complementary to the glenoid surface 224 of the scapula 220, at the site where the glenoid component 222 is to be affixed to the scapula 220. The reverse face 258 is placed against the glenoid surface 224, as described above, and the drill guide 240 is held by the handle 252, for guiding a drill through the first drill guide bore 270 to drill a first hole 300 in the scapula 220. In order to enhance support of the drill during the drilling of the first hole 300, and thus increase the accuracy with which the first hole 300 is drilled, the guide block 250 is provided with a sleeve portion 302 which extends from the obverse face 258 in a direction opposite to the first transverse direction 272 and extends the first drill guide bore 270 for increased support of the drill in accurate alignment with first transverse direction 272.

Once the first hole 300 is completed, a locator pin 310 is coupled with the guide block 250 to project from the reverse face 258, along the first transverse direction 272, as described above in connection with drill guide 40, and the locator pin 310 extending into the first hole 300. In this manner, the second drill guide bore 280 is located in place, relative to the first hole 300, for the drilling of a second hole 320 in the scapula 220, as described above. Subsequently, third and fourth holes 322 and 324 are drilled in the scapula 220, with the third and fourth drill guide bores 290 and 292 serving to guide a drill to complete the drilling of the corresponding third and fourth holes 322 and 324. In the preferred embodiment, a second locator pin 312 is inserted into the second drill guide bore 280 to couple the second locator pin 312 with the guide block 250, with the second locator pin 312 projecting from the guide block 250 in the second transverse direction 282, as illustrated in FIG. 10. With the reverse face 258 seated on the glenoid surface 224, and the locator pins 310 and 312 extending into the first hole 300 and the second hole 320, respectively, in the scapula 220, the guide block 250 is located and stabilized for accurate positioning of the third and fourth drill guide bores 290 and 292 and the concomitant accurate drilling of the third and fourth holes 322 and 324.

It will be seen that the present invention attains the several object and advantages summarized above, namely: Facilitates the location and drilling of holes in the natural bone at the site of a prosthetic implant for appropriate placement and seating of a prosthetic implant component having a specific array of affixation pegs, and especially in connection with the drilling of holes in a scapula for the implant of a glenoid component of a shoulder prosthesis; accommodates the array of affixation pegs in an effective and efficient manner, enabling a reduction in the time necessary to complete an implant procedure, to the benefit of the recipient of the implant; attains increased accuracy with increased ease; provides simplified instruments and procedures for attaining improved results; enables more economical manufacture of effective instruments having a rugged construction for exemplary performance over an extended service life.

It is to be understood that the above detailed description of preferred embodiments of the invention is provided by way of example only. Various details of design, construction and procedure may be modified without departing from the true spirit and scope of the invention, as set forth in the appended claims.

The embodiments of the invention in which an exclusive property or privilege is claimed are defined as follows:

1. A drill guide to be held in place by a surgeon against a scapula for locating holes to be drilled in the scapula at a site for a glenoid component to be affixed to the scapula for providing a bearing for a humeral head in a shoulder prosthesis, with the holes arranged in an array complementary to an array of affixation pegs projecting from the glenoid component, the drill guide comprising:

a guide block having an obverse face and a reverse face, an upper end and a lower end spaced in a longitudinal direction from the upper end, and opposite side edges spaced in lateral directions from one another;

a handle affixed to the guide block for being gripped by the surgeon to hold the guide block in place against the scapula;

a first drill guide bore adjacent the upper end of the guide block and extending in a first transverse direction, transverse to the longitudinal and lateral directions, through the guide block from the obverse face to the reverse face, for guiding a drill to drill a first hole in the scapula along the first transverse direction when the guide block is held in place by the surgeon grieving the handle, with the reverse face of the guide block seated against the scapula at the site for the glenoid component;

a second drill guide bore adjacent the lower end of the guide block and extending in a second transverse direction, transverse to the longitudinal and lateral directions, through the guide block from the obverse face to the reverse face, for guiding a drill to drill a second hole in the scapula along the second transverse direction when the guide block is held in place by the surgeon gripping the handle, with the reverse face of the guide block seated against the scapula at the site for the glenoid component;

at least one locator pin for advancement through one of the first and second drill guide bores in a direction from the obverse face toward the reverse face of the guide block; and coupling means for selectively detachably coupling the locator pin and the guide block in response to advancement of the locator pin through the one of the first and second drill guide bores, with the locator pin projecting from the reverse face of the guide block along at least one of the first and second transverse directions for reception within at least one of the first and second holes drilled in the scapula along a corresponding one of the first and second transverse directions while the guide block is held in place on the scapula so as to locate the other of the first and second transverse directions for drilling the other of the first and second holes in the scapula along the other of the first and second transverse directions, such that the first and second holes are arranged in an array corresponding to the first and second transverse directions and complementary to the array of the affixation pegs of the glenoid component.

2. The invention of claim 1 wherein the reverse face of the guide block includes a surface having a surface contour configuration generally complementary to the scapula at the site for the glenoid component.

3. The invention of claim 2 wherein the guide block includes a sleeve portion projecting from the obverse face of the guide block in a direction opposite the first transverse direction such that the first drill guide bore is extended in the direction opposite to the first transverse direction.

4. The invention of claim 1 wherein the second transverse direction makes an acute angle with the first transverse direction such that the first and second transverse directions diverge in the direction from the obverse face toward the reverse face.

5. The invention of claim 4 wherein the longitudinal and lateral directions essentially lie in a plane, and the first transverse direction extends essentially normal to the plane within which the longitudinal and lateral directions lie.

6. The invention of claim 1 wherein the coupling means include a plug portion on the locator pin, the plug portion being complementary to the first drill guide bore for placement within the first drill guide bore to couple the locator pin with the guide block.

7. The invention of claim 1 wherein the coupling means include a plug portion on the locator pin, the plug portion being complementary to the second drill guide bore for placement within the second drill guide bore to couple the locator pin with the guide block.

8. The invention of claim 1 including:

a third drill guide bore adjacent one of the opposite side edges of the guide block and a fourth drill guide bore adjacent the other of the opposite side edges of the guide block, the third and fourth drill guide bores each being located longitudinally intermediate the first and second drill guide bores and extending through the guide block from the obverse face to the reverse face;

the coupling means including a first plug portion on the first locator pin, the first plug portion being complementary to the first drill guide bore for placement within the first drill guide bore to couple the first locator pin with the guide block, and a second plug portion on the second locator pin, the second plug portion being complementary to the second drill guide bore for placement within the second drill guide bore to couple the second locator pin with the guide block.

9. The invention of claim 8 wherein the second transverse direction makes an acute angle with the first transverse direction such that the first and second transverse directions diverge in the direction from the obverse face toward the reverse face.

10. The invention of claim 9 wherein the longitudinal and lateral directions essentially lie in a plane, and the first transverse direction extends essentially normal to the plane within which the longitudinal and lateral directions lie.

11. A drill guide for locating holes to be drilled in a scapula at a site for a glenoid component to be affixed to the scapula for providing a bearing for a humeral head in a shoulder prosthesis, with the holes arranged in an array complementary to an array of affixation pegs projecting from the glenoid component, the drill guide comprising:

a first guide block having an obverse face and a reverse face, an upper end and a lower end spaced in a longitudinal direction from the upper end, and opposite side edges spaced in lateral directions from one another;

a first drill guide bore adjacent one of the upper end and the lower end of the first guide block and extending in a first transverse direction, transverse to the longitudinal and lateral directions, through the first guide block from the obverse face to the reverse face, for guiding a drill to drill a first hole in the scapula along the first transverse direction when the reverse face of the first guide block is seated against the scapula at the site for the glenoid component;

a second guide block having an obverse face and a reverse face, an upper end and a lower end spaced in a longitudinal direction from the upper end, and opposite side edges spaced in lateral directions from one another;

a second drill guide bore adjacent one of the upper end and the lower end of the second guide block and extending in a second transverse direction, transverse to the longitudinal and lateral directions, through the second guide block from the obverse face to the reverse face, for guiding a drill to drill a second hole in the scapula along the second transverse direction when the reverse face of the second guide block is seated against the scapula at the site for the glenoid component;

a locator pin projecting from the reverse face of the second guide block for reception within one of the first and second holes drilled in the scapula along a corresponding one of the first and second transverse directions to place the second guide block on the scapula and locate the other of the first and second transverse directions for drilling the other of the first and second holes in the scapula along the other of the first and second transverse directions, such that the first and second holes are arranged in an array corresponding to the first and second transverse directions and complementary to the array of the affixation pegs of the glenoid component; and a common handle attached to the first and second guide blocks.

12. The invention of claim 11 wherein the reverse face of each guide block includes a surface having a surface contour configuration generally complementary to the scapula at the site for the glenoid component.

13. The invention of claim 12 wherein at least one of the first and second guide blocks includes a sleeve portion projecting from the obverse face of the guide block in a direction opposite the first transverse direction such that a corresponding one of the first and second drill guide bores is extended in the direction opposite to the first transverse direction.

14. The invention of claim 11 wherein the second transverse direction makes an acute angle with the first transverse direction such that the first and second transverse directions diverge in the direction from the obverse face toward the reverse face of the second guide block.

15. The invention of claim 14 wherein the longitudinal and lateral directions essentially lie in a plane, and the first transverse direction extends essentially normal to the plane within which the longitudinal and lateral directions lie.

16. The invention of claim 15 wherein the locator pin projects adjacent the upper end of the second guide block and the second drill guide bore is located adjacent the lower end of the second guide block.

17. A drill guide to be held in place by a surgeon against natural bone for locating holes to be drilled in the natural bone at a site for a prosthetic implant component to be affixed to the natural bone, with the holes arranged in an array complementary to an array of affixation pegs projecting from the prosthetic implant component, the drill guide comprising:

a guide block having an obverse face and a reverse face, an upper end and a lower end spaced in a longitudinal direction from the upper end, and opposite side edges spaced in lateral directions from one another;

a handle affixed to the guide block for being gripped by the surgeon to hold the guide block in place against the natural bone;

a first drill guide bore adjacent the upper end of the guide block and extending in a first transverse direction, transverse to the longitudinal and lateral directions, through the guide block from the obverse face to the reverse face, for guiding a drill to drill a first hole in the natural bone along the first transverse direction when the guide block is held in place by the surgeon gripping the handle, with the reverse face of the guide block seated against the natural bone at the site for the prosthetic implant component;

a second drill guide bore adjacent the lower end of the guide block and extending in a second transverse direction, transverse to the longitudinal and lateral directions, through the guide block from the obverse face to the reverse face, for guiding a drill to drill a second hole in the natural bone along the second transverse direction when the guide block is held in place by the surgeon gripping the handle, with the reverse face of the guide block seated against the natural bone at the site for the prosthetic implant component;

at least one locator pin for advancement through one of the first and second drill guide bores in a direction from the obverse face toward the reverse face of the guide block; and coupling means for selectively detachably coupling the locator pin and the guide block in response to advancement of the locator pin through the one of the first and second drill guide bores, with the locator pin projecting from the reverse face of the guide block along at least one of the first and second transverse directions for reception within at least one of the first and second holes drilled in the natural bone along a corresponding one of the first and second transverse directions while the guide block is held in place on the natural bone so as to locate the other of the first and second transverse directions for drilling the other of the first and second holes in the natural bone along the other of the first and second transverse directions, such that the first and second holes are arranged in an array corresponding to the first and second transverse directions and complementary to the array of the affixation pegs of the prosthetic implant component.

18. The invention of claim 17 wherein the second transverse direction makes an acute angle with the first transverse direction.

19. The invention of claim 18 wherein the first and second transverse directions diverge in the direction from the obverse face toward the reverse face.

20. A method for implanting a glenoid component of a shoulder prosthesis, the method including locating holes to be drilled in a scapula at a site for the glenoid component to be affixed to the scapula for providing a bearing for a humeral head in the shoulder prosthesis, the glenoid component including affixation pegs projecting from the glenoid component in an array, the method comprising:
    seating the reverse face of a guide block against the scapula at the site for the glenoid component, the guide block having an obverse face and a reverse face, an upper end and a lower end spaced in a longitudinal direction from the upper end, and opposite side edges spaced in lateral directions from one another;
    drilling a first hole in the scapula by guiding a drill through one of a first drill guide bore adjacent the upper end of the guide block and extending in a first transverse direction transverse to the longitudinal and lateral directions, through the guide block from the obverse face to the reverse face, and a second drill guide bore adjacent the lower end of the guide block and extending in a second transverse direction transverse to the longitudinal and lateral directions, through the guide block from the obverse face to the reverse face;
    advancing a locator pin through the one of the first and second drill guide bores in a direction from the obverse face toward the reverse face of the guide block and into the first hole in the scapula while the guide block is seated against the scapula;
    coupling the locator pin with the guide block, with the locator pin projecting from the reverse face of the guide block along one of the first and second transverse directions for reception within the first hole and the reverse face of the guide block seated on the scapula to locate the other of the first and second transverse directions relative to the scapula;
    drilling a second hole in the scapula by guiding a drill through the other of the first and second drill guide bores such that the first and second holes are arranged in an array corresponding to the first and second transverse directions and complementary to the array of the affixation pegs of the glenoid component;
    retracting the guide block from the scapula; and
    affixing the glenoid component to the scapula at the site, with the affixation pegs inserted into the first and second holes.

21. The invention of claim 20 wherein the glenoid component includes further affixation pegs projecting from the glenoid component, and the guide block includes a third drill guide bore intermediate the upper and lower ends and adjacent one of the opposite side edges of the guide block, the third drill guide bore extending from the obverse face to the reverse face along a third transverse direction, and a fourth drill guide bore intermediate the upper and lower ends and adjacent the other of the opposite side edges of the guide block, the fourth drill guide bore extending from the obverse face to the reverse face along a fourth transverse direction, the method including:
    advancing a further locator pin through the other of the first and second drill guide bores in a direction from the obverse face toward the reverse face of the guide block into the second hole in the scapula while the guide block is seated against the scapula;
    coupling the further locator pin with the guide blocks, with the further locator pin projecting from the reverse face of the guide block along the other of the first and second transverse directions for reception within the second hole and the reverse face of the guide block seated on the scapula to locate third and fourth transverse directions; and
    drilling a third hole in the scapula by guiding a drill through the third drill guide bore, and drilling a fourth hole in the scapula by guiding a drill through the fourth drill guide bore such that the first, second, third and fourth holes are arranged in an array complementary to the array of the affixation pegs of the glenoid component.

22. A method for implanting a prosthetic implant component, the method including locating holes to be drilled in the natural bone at a site for the prosthetic implant component, the prosthetic implant component including affixation pegs projecting from the prosthetic implant component in an array, the method comprising:
    seating the reverse face of a guide block against the natural bone at the site for the prosthetic implant component, the guide block having an obverse face and a reverse face, an upper end and a lower end spaced in a longitudinal direction from the upper end, and opposite side edges spaced in lateral directions from one another;
    drilling a first hole in the natural bone by guiding a drill through one of a first drill guide bore adjacent the upper end of the guide block and extending in a first transverse direction transverse to the longitudinal and lateral directions, through the guide block from the obverse face to the reverse face, and a second drill guide bore adjacent the lower end of the guide block and extending in a second transverse direction transverse to the longitudinal and lateral directions, through the guide block from the obverse face to the reverse face;
    advancing a locator pin through the one of the first and second drill guide bores in a direction from the obverse face toward the reverse face of the guide block and into the first hole in the natural bone while the guide block is seated against the natural bone;
    coupling the locator pin with the guide block, with the locator pin projecting from the reverse face of the guide block along one of the first and second transverse directions for reception within the first hole and the reverse face of the guide block seated on the natural bone to locate the other of the first and second transverse directions relative to the natural bone;

drilling a second hole in the natural bone by guiding a drill through the other of the first and second drill guide bores such that the first and second holes are arranged in an array corresponding to the first and second transverse directions and complementary to the array of the affixation pegs of the prosthetic implant component;

retracting the guide block from the natural bone; and
affixing the prosthetic implant component to the natural bone at the site, with the affixation pegs inserted into the first and second holes.

* * * * *